United States Patent [19]

Reiner

[11] 4,412,996
[45] * Nov. 1, 1983

[54] PYRIDOXINE DERIVATIVES AND RELATED PHARMACEUTICAL COMPOSITIONS

[75] Inventor: Alberto Reiner, Como, Italy

[73] Assignee: Crinos Farmacologica Spa, Como, Italy

[*] Notice: The portion of the term of this patent subsequent to Apr. 7, 1998, has been disclaimed.

[21] Appl. No.: 313,311

[22] Filed: Oct. 20, 1981

[30] Foreign Application Priority Data

Oct. 21, 1980 [IT] Italy ............................... 25473 A/80

[51] Int. Cl.³ ................ A61K 31/435; C07D 401/112; C07D 213/67
[52] U.S. Cl. .................................... 424/256; 424/263; 546/116; 546/273; 546/302
[58] Field of Search ....................... 546/116, 273, 302; 424/256, 263

[56] References Cited

U.S. PATENT DOCUMENTS 4,165,428  8/1979  Noda et al. ..................... 546/273
4,233,304  11/1980  Reiner ............................. 546/116

OTHER PUBLICATIONS

Merck Index, (1976) p. 4840.

*Primary Examiner*—John M. Ford
*Assistant Examiner*—Bernard Dentz
*Attorney, Agent, or Firm*—Murray and Whisenhunt

[57] ABSTRACT

The esters of pyridoxine and of isopropylidene pyridoxine with 1-(p-chlorobenzoyl)-2-methyl-5-methoxy-indol-3-acetic acid and 5-(2,4-difluorophenyl)-salicylic acid are essentially endowed with the same activities of the corresponding acids and are less toxic and gastrolesive, whereby the therapeutical index is remarkably improved. For the preparation of these compounds the chloride of the acid is reacted with isopropylidene pyridoxine, followed by a hydrolysis to obtain the corresponding pyridoxine derivative.

10 Claims, No Drawings

PYRIDOXINE DERIVATIVES AND RELATED PHARMACEUTICAL COMPOSITIONS

The present invention relates to therepeutically active derivatives of pyridoxine and isopropylidene pyridoxine, having general formula:

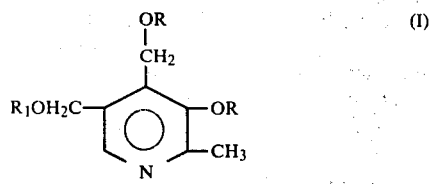

wherein R represents hydrogen or, in combination, an isopropylidene group, and $R_1$ represents the residue of an acid of the group comprising 1-(p-cholorobenzoyl)-2-methyl-5-methoxy-indol-3-acetic acid and 5-(2,4-difluorophenyl)-salicylic acid, and the related salts with inorganic and organic, non toxic and pharmaceutically acceptable acids.

The 1-(p-chlolobenzoyl)-2-methyl-5-methoxy-indol-3-acetic acid, also known with the generical name of "Indomethacin", is endowed with remarkable anti-inflammatory, anti-phlogistic and analgesic properties and activities, which however are accompanied by not negligible phenomena of gastric intolerance and ulcerogenicity as well as of relevant toxicity, whereby the use thereof is seriously limited, especially in the case of extended treatments, and particular cautions and controls are anyhow necessary.

A like problem, although in a different magnitude, exists for the 5-(2,4-difluorophenyl)-salicylic acid, also known under the non chemical name of "Diflunisal".

An indication of the problems and difficulties related to the aforesaid active principles can be obtained from the fact that, despite their high activity (Indomethacin is often taken as the reference comparison compound for the evaluation of the anti-inflammatory activity of other compounds), these drugs are used in the more serious cases, when other less toxic active substances fails as regards the therapeutical aim.

It has been now found that the esters according to the present invention maintain the therapeutical properties of the free acids, especially as regards the analgesic activity, but show relevantly reduced toxicity and gastrolesivity, whereby the therapeutical index is remarkably improved in comparison with the free acid.

Another feature of the present invention resides in the process for the preparation of esters of pyridoxine and isopropylidene pyridoxine, particularly of the compounds of the invention.

Such a process, in fact, comprises the reaction, in an anhydrous and inert solvent, of isopropylidene pyridoxine with the chloride of the acid, in the presence of an acid separator, particularly a tertiary amine, as the catalyst, and the hydrolysis step when the desired derivative is the pyridoxine ester.

In turn of the hydrolysis should be carried out, according to the methods known in the art, (as in the case of like compounds) in acidic environment and in hot condition.

However, in the case of the pyridoxine ester of 1-(p-chlorobenzoyl)-2-methyl-5-methoxy-indol-3-acetic acid, the carrying out of the hydrolysis under the standard conditions for the conversion from isopropylidene pyridoxine into pyridoxine ester would not only lead to the removal of the isopropylidene group, which is a desired occurrence, but also to the splitting of the p-chlorobenzoic group, which is not desired, with the easily understandable consequences.

Another problem related to the known process of acidic hydrolysis and relating not only to the pyridoxine ester of Indomethacin, but to all esters of pyridoxine with organic acids, particularly with 5-(2,4-difluorophenyl)-salicylic acid, 2-hydroxybenzoyl acid, 2-(2,3-dimethylphenyl)-amino-benzoic acid, 4-allyloxy-3-chloro-phenylacetic acid, 2-(3-benzoylphenyl)-propionic acid, 2-(4-isobutylphenyl)-propionic acid, d-2(6-methoxy-2-naphtyl)-propionic acid, 2-(6-methoxy-2-naphtyl)-propionic acid, 2-3-(trifluoromethyl)-phenylamino-benzoic acid and 2-3-(trifluoromethyl)-phenylamino-nicotinic acid, is that of the relatively low yields and of the presence of by-products and impurities which are objectionable from the point of view of the industrial production and cause expensive and time-consuming purification treatments to be necessarily carried out for the pharmaceutical use.

It has been now found and is another object of the present invention that the problems and disadvantages, as above shortly mentioned, are substantially done away with a process of acidic hydrolysis characterized in that the hydrochloride of the ester of isopropylidene pyridoxine with an acid selected in the previously indicated group is refluxed in a hydro-alcoholic medium for the time needed for the reaction to be completed. It has been particularly found that the hydro-alcoholic medium is advantageously formed a mixture of water and of a lower aliphatic alcohol, in a ratio water/alcohol of between 1:2 and 1:5 by volume, the reaction mixture being maintained under stirring for an extended time of the order of some hours, until the hydrolysis is completed. The desired raw product is thereby obtained and is crystallized from a solvent, preferably methylisobutylketone, with high yields and purity.

In the following examples, having illustrative but not limitative purpose, the preparation of the compounds of the invention is described:

EXAMPLE 1

Isopropylidene pyridoxine ester of 1-(p-chlorobenzoyl)-2-methyl-5-methoxy-indol-3-acetic acid

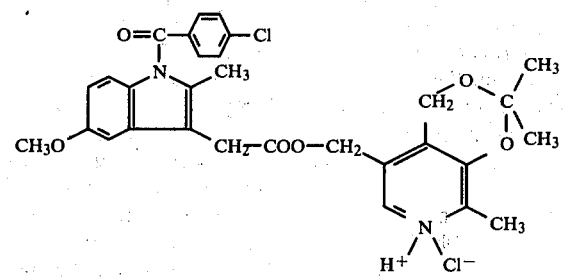

(a) chloride of the 1-(p-chlorobenzoyl)-2-methyl-5-methoxy-indol-3-acetic acid.

A glass flask is charged with 900 mls of benzene, 159 g of thionyl chloride and 400 g of 1-(p-chlorobenzoyl)-2-methyl-5-methoxy-indol-3-acetic acid, and a fluid stirrable mass is obtained, which is heated in a water bath up to a temperature of 65° C. Within about 4 hours the end of the gas development is observed in a gas trap.

The reaction mass is cooled and the crystallized chloride is filtered in a porous filter. It is washed with cold benzene and dried under vacuum. From the filtration mother liquors, after concentration, further chloride crystallizes.

There are obtained 322 g of chloride of the 1-(p-chlorobenzoyl)-2-methyl-5-methoxy-indol-3-acetic acid with a yield of 76%.

(b) Hydrochloride of the (3,4-isopropylidene)-pyridoxine ester of 1-(p-chlorobenzoyl)-2-methyl-5-methoxy-indol-3-acetic acid.

In a three neck glass flask, having stirrer, thermometer and cooler, 320 g of the chloride obtained in the step (a) are charged and are dissolved in 670 mls of anhydrous chloroform. The temperature of the solution is reduced, by means of external brine, to 4° C.

A solution of 178 g of (3,4-isopropylidene)-pyridoxine dissolved in 500 mls of chloroform is separately prepared and added with 96 g of triethylamine. The temperature of the solution is reduced to 4° C. and the addition of the chloride solution is slowly started, care being taken that the reaction temperature does not overcome the value of 10° C. Upon the addition is completed, the reaction mixture is maintained under stirring for 20 hours, and the temperature slowly increases up to 20° C. within about 12 hours.

The reaction mixture is then washed with water, with water made acidic with HCl, with water supplemented with sodium carbonate and lastly with water again. The chloroformic extract is separated in a flask, dried over $Na_2SO_4$ and concentrated.

A greenish oil is obtained, which is dissolved with methylisobutylketone and slowly crystallized; it is then filtered and converted to the hydrochloride by taking the mass with anhydrous acetone and bubbling gaseous hydrogen chloride.

326 g of product having melting point of 180°-190° C. (yield: 65% of the theoretical value) are obtained, it being soluble in cold chloroform and in hot ethanol; the product is poorly soluble in hot N,N'-dimethylformamide and insoluble in water.

(c) (3,4-isopropylidene)-pyridoxine ester of 1-(p-chlorobenzoyl)-2-methyl-5-methoxy-indol-3-acetic acid. 50 g of the ester hydrochloride as obtained in the step (b) are added to a mixture of 550 mls of methylisobutylketone and 250 mls of water.

7 mls of 33% $NH_4OH$ are added. The active compound is completely dissolved and from the solution, after concentration to dryness, an oil is obtained which, by adding 100 mls of ethanol (95° C.), does completely crystallize. There are obtained 36 g of a product having melting point of 106°-107° C., having a unique chromatographic spot. By operating in the same manner the corresponding esters of the 5-(2.4-difluorophenyl)-salicylic acid are obtained, with the following properties:

(1) 5-(2,4-difluoro-phenyl)-salicyloyl ester of (3.4-isopropylidene)-pyridoxine hydrochloride, having melting point of 172°-173° C., which by chromatographic analysis is in pure form and in accordance with the reference data.

(2) 5-(2,4-difluorophenyl)-salicyloyl ester of (3,4-isopropyliden)-pyridoxine having melting point of 99°-102° C., in form of white, microcrystalline powder. The U.V., I.R. and N.M.R. spectra correspond to the theoretical data.

EXAMPLE 2

Pyridoxine ester of 1-(p-chlorobenzoyl)-2-methyl-5-methoxy-indol-3-acetic acid

This example specifically relates to the hydrolysis step with exclusive removal of the isopropylidene group. In a glass flask, having stirrer and cooler, 120 g of the hydrochloride obtained in the step (b) of Example 1 are charged together with 1000 mls of methanol of technical grade and 250 mls of water.

The mixture is refluxed for 10 hours (at about 65° C.), the hydrolysis pattern being monitored by chromatography.

The mixture is cooled and then poured into about 1500 mls of water-ammonia solution, whereby the raw hydrolized product precipitates, having melting point of 79°-80° C.

The product is then crystallized from methylisobutylketone, after passing onto decoloring charcoal, and there are obtained 75 g of product with a yield of 72% of the theoretical value and with a melting point of 145°-147° C.

EXAMPLE 3

Pyridoxine ester of 5-(2.4-difluorophenyl)-salycylic acid

In a 1000 ml flask, having a stirrer, a thermometer and a heating bath, 50 g of 5-(2.4-difluorophenyls)-salicyloyl ester of (3.4-isopropylidene)-pyridoxine hydrochloride are charged and added with 500 mls of methanol and 125 mls of water.

The reaction mixture is refluxed, the reaction being monitored by taking samples for the chromatographic assay.

After 6 hour reaction, the resulting mixture, in form of heterogeneous solution, is poured into 2000 mls of water under stirring, ammonia being then added. There are obtained 32 g of raw product which are crystallized from methylisobutylketone and filtered, thus forming 13.7 g of a pure product, which is in accordance with the standard data of the chromatographic analysis, having melting point 167°-170° C.

The compounds of the invention have been subjected to pharmacological and toxicological investigations, which revealed that, in comparison with the free acids, there are achieved those highly desirable results of lower toxicity and greater gastric tolerability, the therapeutical activity remaining unchanged. In the following resuming table the results obtained for the esters of the Indomethacin are reported. In the determination of the acute toxicity, carried out in the rat, the method of Litchfield and Wilcoxon (J. Pharmacol. Exp. Therm., 96, 99, 1949) has been adopted.

As regards the analgesic activity, the evaluation has been carried out according to the method of Randall and Selitto (Arch. Ing. Pharmacodyn., 111, 409, 1949).

As regards the anti-inflammatory activity, the $ED_{50}$ in the normal rat has been evaluated according to Winter et al. (Proc. Soc. Exp. Biol. Med., 111, 544, 1962).

Lastly, with respect to the ulterogenic acitivty, indicated as $UD_{50}$, it has been determined by administering per os the compounds to fasted rats and evaluating the presence of gastric lesions at predetermined times after the administration.

The $UD_{50}$ has been also calculated according to the aforesaid method of Litchfield and Wilcoxon.

TABLE

| | Indomethacin | compound ex. 2 (62.5%* at 819mg/kg) | compound ex. 1(c) >200* mg/kg | compound ex. 1(b) |
|---|---|---|---|---|
| $LD_{50}$, rat mg/kg/os | 21 | | | 85 |
| Carrageenin induced oedema (3 h) $ED_{50}$ mg/kg/os | 4.40 | 75.98 | 36.83 | 10.13 |
| Therapeutical index $LD_{50}/ED_{50}$ (carrageenin 3h) | 4.77 | | | 8.39 |
| Randall-Selitto (3 h) $ED_{50}$ mg/kg/os | 1.33 | 3.37 | 2.70 | 2.66 |
| Therapeutical index $LD_{50}/ED_{50}$ (Randall-Selitto 3h) | 15.78 | | | 31.95 |
| Gastric tolerability $UD_{50}$ fasted 48 h | 3.45 | 285.00 | 140.00 | 22.50 |
| Tolerability index $UD_{50}$ (48 h)/$ED_{50}$ (carrageenin 3 h) | 0.78 | 3.75 | 3.80 | 2.22 |
| Tolerability index $UD_{50}$ (48 h)/$ED_{50}$ (Randall-Selitto 3 h) | 2.59 | 84.56 | 51.85 | 8.45 |
| Gastric tolerability $UD_{50}$ fasted 18 h | 6.90 | 530.00 | 212.00 | 33.50 |
| Tolerability index $UD_{50}$ (18 h)/$ED_{50}$ (carrageenin 3 h) | 1.57 | 6.97 | 5.75 | 3.30 |
| Tolerability index $UD_{50}$ (18h)/$ED_{50}$ (Randall-Selitto 3 H) | 5.18 | 157.27 | 78.51 | 12.59 |

*Insufficient sample

The present invention is further directed to pharmaceutical compositions containing, as the active principle, a compound of formula (I) in combination with a pharmaceutical excipient or vehicle, and formulated for the oral, parenteral, rectal or topical administration.

The compositions for the oral administration can be in solid form (capsules, tablets, pills, together with excipients such as lactose, starch, talc, magnesium stearate) or in liquid form (syrups, drops, suspensions, with suitable liquid vehicles comprising water and sweetening, flavoring, dispersing and/or other agents).

The compositions for the parenteral administration consist of injectable solutions, either aqueous (comprising also mixtures of water and glycols) and oily.

For the oral and parenteral administration forms, the compounds of the invention are preferably used as an addition salt with a non toxic and pharmaceutically acceptable acid, such as for instance hydrochlorides, hydrobromides, sulfates, acetates, succinates, fumarates, tartrates, salicylates, nicotinates etc.

For the rectal and topical preparations there are lastly used standard bases for suppositories and, respectively, for creams and ointments.

The pharmaceutical compositions of the present invention are preferably formulated so as to permit a untary dose of the active principle to be administered, consistently with the efficacy of the active compound and with the desired effect.

The unitary doses of the active principle for the oral and parenteral administration can be suitably comprised between 100 and 1000 mg, preferably between 250 and 700 mg, whereas those for rectal administration can be comprised between 200 and 1500 mg, preferably between 500 and 1000 mg lastly, for the topical application, the concentration of the active principle by weight is of between 1 and 10%, and preferably is 5%.

I claim:

1. A derivative of pyridoxine and isopropylidene pyridoxine having the formula:

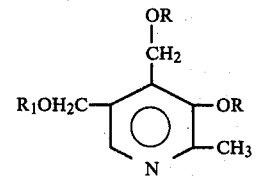

wherein the R radicals represent a hydrogen atom or, conjointly, an isopropylidene group, and $R_1$ represents the residue of an acid selected in the group comprising 1-(p-chlorobenzoyl)-2-methyl-5-methoxy-indol-3-acetic acid and 5-(2.4-difluorophenyl)-salicylic acid, and the related addition salts with non toxic and pharmaceutically acceptable, inorganic and organic acids.

2. A derivative according to claim 1, in form of hydrochlorides, hydrobromides, sulfates, acetates, succinates, maleates, fumarates, tartrates, salicylates, cyclohexylsulfamates, nicotinates.

3. Derivative of claim 1, wherein said derivative is isopropylidene pyridoxine ester of 1-(p-chlorobenzoyl)-2-methyl-5-methoxy-indol-3-acetic acid or a pharmaceutically acceptable addition salt thereof.

4. Derivative of claim 1, wherein said derivative is pyridoxine ester of 1-(p-chlorobenzoyl)-2-methyl-5-methoxy-indol-3-acetic acid or a pharmaceutically acceptable addition salt thereof.

5. Derivative of claim 1, wherein said derivative is pyridoxine ester of 5-(2,4-difluorophenyl)-salicylic acid or a pharmaceutically acceptable addition salt thereof.

6. An anti-inflammatory compositon comprising an anti-inflammatory amount of a derivative of pyroxidine or of isopropylidene pyridoxine according to one of claims 1, 3, 4 or 5, together with pharmaceutically acceptable excipients and/or vehicles.

7. Composition according to claim 6, in a form suitable for oral administration.

8. Composition according to claim 6, in form suitable for parenteral administration.

9. Composition according to claim 6, in form suitable for rectal administration.

10. Composition according to claim 6, in form suitable for topical application.

* * * * *

UNITED STATES PATENT AND TRADEMARK OFFICE
CERTIFICATE OF CORRECTION

PATENT NO. : 4,412,996
DATED : November 1, 1983
INVENTOR(S) : Alberto Reiner

It is certified that error appears in the above-identified patent and that said Letters Patent is hereby corrected as shown below:

In the title page, correct the name of the assignee to read Crinos Industria Farmacologica Spa.

Signed and Sealed this

Fourth Day of November, 1986

[SEAL]

Attest:

DONALD J. QUIGG

Attesting Officer

Commissioner of Patents and Trademarks